United States Patent [19]

Coston

[11] Patent Number: 4,626,211
[45] Date of Patent: Dec. 2, 1986

[54] DENTAL SHIELD
[76] Inventor: Cindy Coston, 11614 Veradero, San Antonio, Tex. 78216
[21] Appl. No.: 778,400
[22] Filed: Sep. 20, 1985
[51] Int. Cl.⁴ ............................................. A61C 5/14
[52] U.S. Cl. .................................... 433/137; 433/136
[58] Field of Search ........................ 433/136, 137, 138
[56] References Cited

U.S. PATENT DOCUMENTS 465,265  12/1891  Hansen ............................... 433/137
2,081,779  5/1937  Titus .................................... 433/137
4,344,758  8/1982  Wielhouwer et al. .............. 433/137

Primary Examiner—John J. Wilson

[57] ABSTRACT

This dental shield is designed to protect a patient against the breathing and facial deposit of the powder/water spray from a teeth clean apparatus. Primarily, it consists of a plastic backed two-ply paper panel, having a cotton mouth guard, a cotton nose guard, and a filter rib for filtering the air breathed by the patient.

1 Claim, 3 Drawing Figures

DENTAL SHIELD

BACKGROUND OF THE INVENTION

1. Field of the Invention

This invention relates to face protection devices, and, more particularly, to a dental shield.

2. Description of the Prior Art

In the modern process of teeth cleaning, an airabrasive method of tooth polishing is employed, which is called the Prophy-Jet method that uses baking soda powder to blast away heavy stain, resulting in a smooth polished surfaces. Once the apparatus is activated by a foot pedal, the powder/water spray emits a fine aerosol of baking soda which the patient breathes and, upon completion of the procedure, a fine layer of powder is left on the patient's face. This powder also causes itching in some people, and the only means of providing protection in the prior art, is the employment of a cloth towel draped over the nose and eyes of the patient, and the dental hygienist is recommended to wear gloves, mask, and eyeglasses for his protection.

References are the U.S. patents of Wielhouwer et al 4,344,758, Hesselgren 3,781,994, McConville 3,662,466, and Carl-Axel Gross 3,478,432.

The principal object of this invention is to provide a dental shield, which will be of such design, as to provide excellent protection for patients, against breathing in the fine aerosol of baking soda when they are having their teeth cleaned by the currently used powder/water spray that blasts away heavy stain on a patient's teeth.

Another object of this invention is to provide a dental shield, which will comprise a two-ply plastic backed paper panel having a mouth opening therein, a mouth guard and a nose guard of cotton and the panel will cover the patient's face to also protect it against powder accumulation thereon.

SUMMARY OF THE INVENTION

Figure 1:
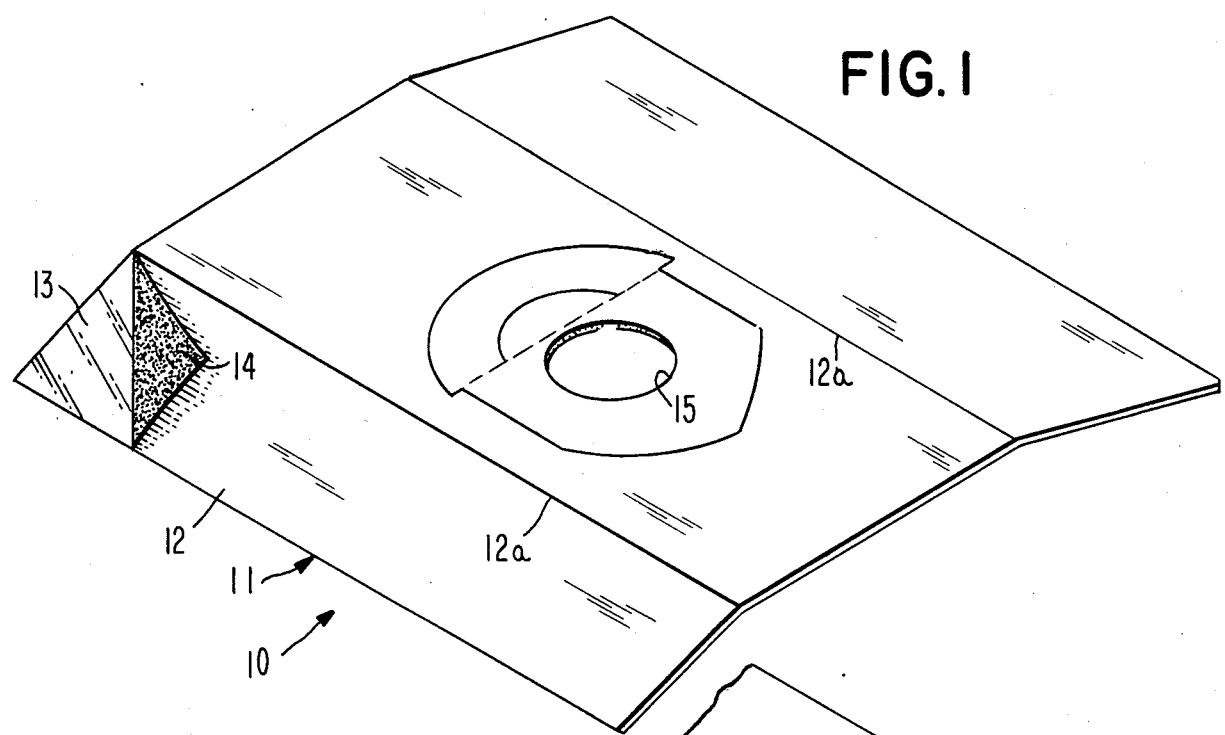
FIG. 1 is a perspective view of the present invention.
Figure 2:
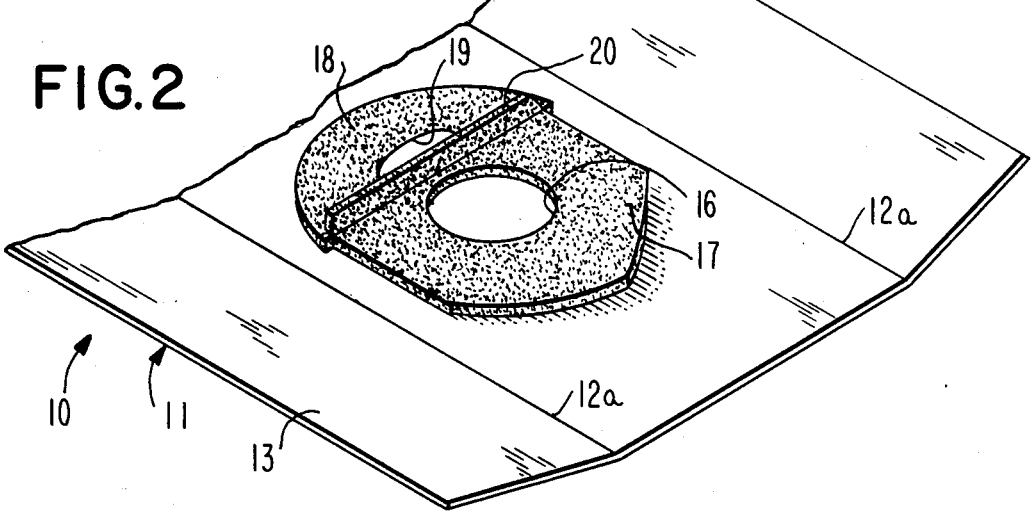
FIG. 2 is a fragmentary bottom perspective view of the invention.

A dental shield for protecting a patient from breathing in the fine aerosol powder/water spray employed to clean and polish teeth, comprising a two-ply paper panel backed by a sheet of plastic. An opening is provided in the panel which aligns with a similar opening provided through a cotton mouth guard, and a cotton nose guard is also provided, with rib deflection and filter means.

DETAILED DESCRIPTION

Accordingly, a shield 10 is shown to include a panel 11 composed of a two-ply sheet of paper 12, having a plastic sheet adhered to its back by means of adhesive 14. A mouth opening 15 is provided through panel 11 which aligns with a similar mouth opening 16 through a cotton mouth guard 17. Mouth guard 17 is of cotton for absorbing purposes and is suitably adhered to the rear side of panel 11 for engagement with a patient's face, and the openings 15 and 17 enable the dental hygienist to enter the instrument that is used to clean and polish the patient's teeth. A nose guard 18 is provided and is also of cotton, and includes an opening 19 at its lower edge for the reception of the patient's nose, and nose guard 18 is also adhered to the rear of panel 11. A cotton rib 20 is horizontally disposed and adhered to the base portion of nose guard 18 and provides filter means against the inhalation of the fine aerosol spray of powder/water.

In use, shield 10 is placed over the patient's face with the openings 15 and 16 encompassing the patient's mouth, and the nose of the patient fits into the nose guard 18 with the nostrils of the patient facing the cotton rib 20 which filters the air being breathed. When the cleaning of the patient's teeth has been completed, the shield 10 is discarded.

Figure 3:
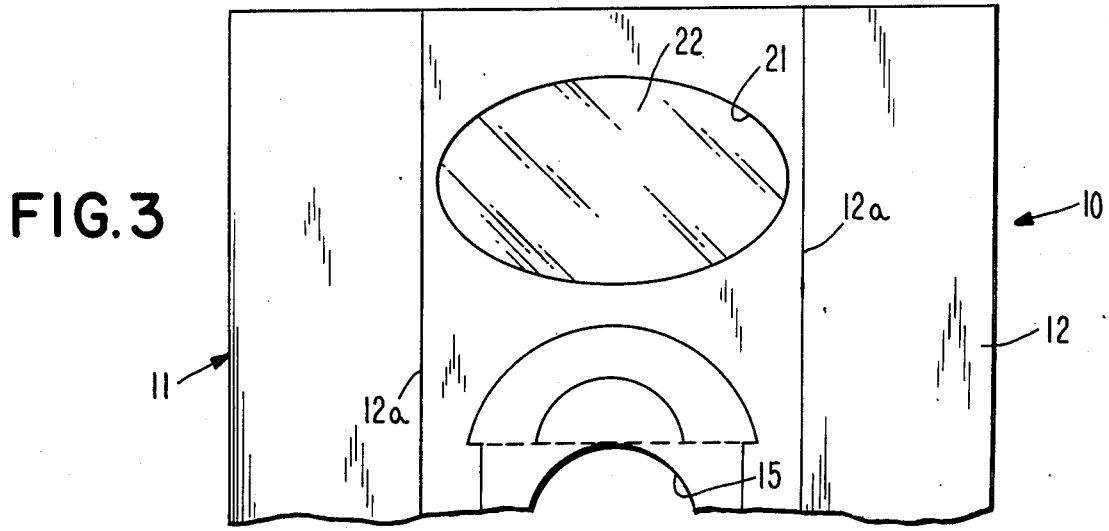
FIG. 3 is a fragmentary front elevational view of the invention, shown modified.

Looking now at FIG. 3, shield 10 is modified to include an upper opening through panel 11, in which is fixedly secured a clear plastic window, so as to enable the patient to see through panel 11.

In use, the function of shield 10 remains the same, with the exception of the window 22 being added, which may make a patient more comfortable, because they can see outside.

While various changes may be made in the detail construction, it is understood that such changes will be within the spirit and scope of the present invention, as is defined by the appended claims.

What I now claim is:

1. A dental shield, comprising, in combination, a panel, a mouth gaurd secured to said panel, a nose guard secured to said panel and a filtering rib secured to said panel; an opening being formed through said panel and aligned with a similar opening through said mouth guard, said mouth guard being fabricated of cotton, and both the opening through said panel and the opening through said mouth guard enabling the entry of a tooth cleaning and polishing instrument therethrough; one face of said mouth guard being fixedly adhered to a rear face of said panel and the opening through said mouth guard encompasing a patient's mouth; said nose guard being fabricated of cotton and having a recess in its bottom for fitting therein a nose of said patient, and one face of said nose guard being fixedly adhered to said rear face of said panel; and said filtering rib being fabricated of cotton and being horizontally disposed and fixedly adhered to a bottom of said nose guard and projecting under the nostrils of said patient and filtering the air being threatened by said patient.

* * * * *